United States Patent [19]

Wolters et al.

[11] Patent Number: 5,442,858
[45] Date of Patent: Aug. 22, 1995

[54] AUTOMATED ANGLE ENCODER SYSTEM FOR MRI APPARATUS

[75] Inventors: Harrie J. M. Wolters, Menlo Park; Philip M. Brooks, Foster City; David T. H. Hung, Palo Alto; Richard C. Motamedi, Sunnyvale; Louis S. Rosinski, Jr., Simi Valley, all of Calif.

[73] Assignee: Resonex Holding Company, Fremont, Calif.

[21] Appl. No.: 157,389

[22] Filed: Nov. 23, 1993

Related U.S. Application Data

[63] Continuation of Ser. No. 979,532, Nov. 23, 1992.

[51] Int. Cl.⁶ .................................. G01B 11/14
[52] U.S. Cl. ........................... 33/1 N; 33/707; 128/782
[58] Field of Search ............ 33/1 N, 1 PT, 511, 512, 33/515, 534, 706, 707; 128/774, 779, 782

[56] References Cited

U.S. PATENT DOCUMENTS

| | | | |
|---|---|---|---|
| 1,590,499 | 6/1926 | Cozad | 128/782 |
| 4,571,834 | 2/1986 | Fraser et al. | 33/512 |
| 4,771,548 | 9/1988 | Donnery | 33/1 N |
| 4,834,057 | 5/1989 | McLeod, Jr. | 33/512 |
| 4,940,063 | 7/1990 | Challis | 33/512 |
| 5,129,725 | 7/1992 | Ishizuka et al. | 33/707 |
| 5,163,228 | 11/1992 | Edwards et al. | 33/1 N |

OTHER PUBLICATIONS

*Motion*, "fiber Optic Encoders", Mar./Apr. 1992, pp. 3–4.
A portion of a book chapter 8 entitled "Kinematics of the Cervical Spine", pp. 174–176 (no date).

*Primary Examiner*—William A. Cuchlinski, Jr.
*Assistant Examiner*—G. Bradley Bennett
*Attorney, Agent, or Firm*—Flehr, Hohbach, Test, Albritton & Herbert

[57] ABSTRACT

An automated angle encoder system for magnetic resonance (MRI) apparatus includes a removable encoder device placed on the orthopedic positioning device which is made entirely of nonmagnetic, nonmetallic materials and includes a glass disk which provides a GRAY output code to indicate absolute angle. The casing is made of Delrin plastic and the fiber optic cable includes nonmetallic TEFLON sheathing. Associated computer apparatus provides for an automatic input of an angle offset to provide for a neutral starting position and also for positive or negative angles of movement.

6 Claims, 8 Drawing Sheets

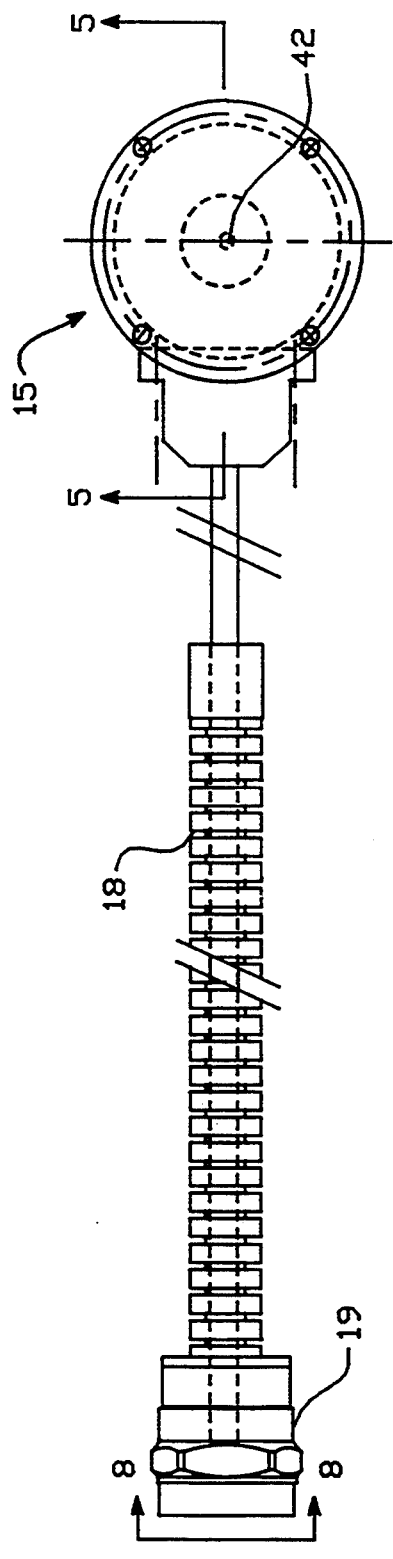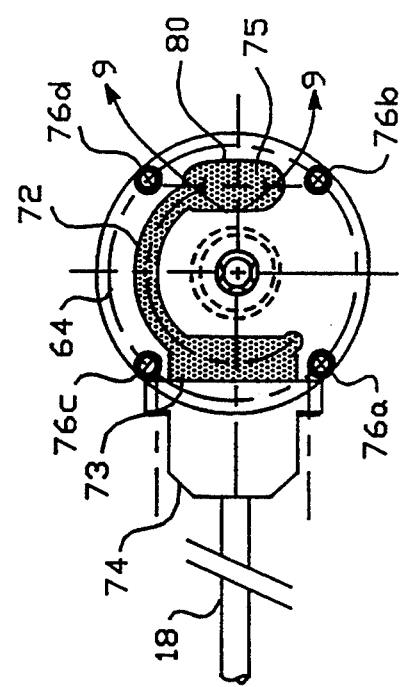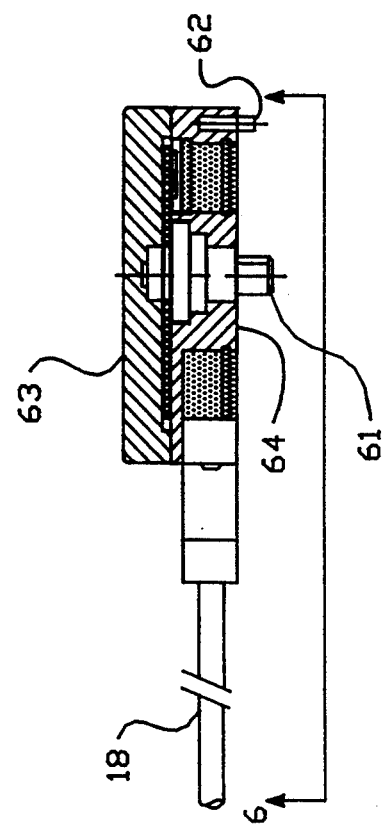

To Fig. 10B

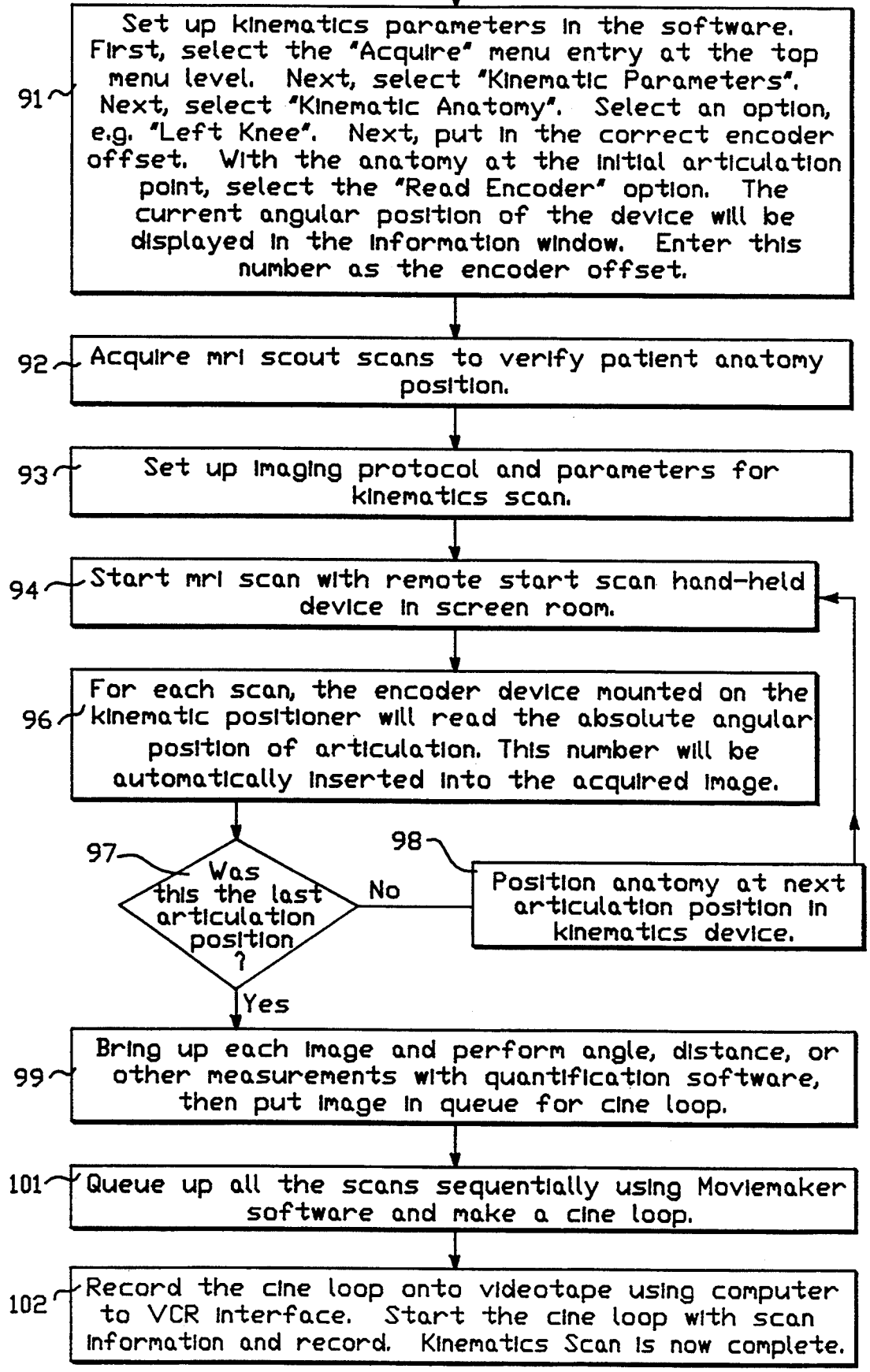

AUTOMATED ANGLE ENCODER SYSTEM FOR MRI APPARATUS

RELATED APPLICATION

This is a continuation application of Ser. No. 07/979,532, filed Nov. 23, 1992.

The present invention is directed to an automated angle encoding system for MRI apparatus.

BACKGROUND OF THE INVENTION

Kinematic MRI imaging of various body joints such as the knee has been done before, as for example, by some type of positioning device. One type of knee positioning device is disclosed and claimed in co-pending application Ser. No. 07/979,532, filed Nov. 23, 1992, in the names of Kriedler et al. Besides manipulating or articulating two body parts in the aperture of the MRI apparatus by the above orthopedic positioning device, it is necessary to measure the intermittent or successive angles of several positions. In the above application the positioning device is connected to a digital readout type encoder device. However, for optimum results, the encoder must not interfere with the existing magnetic fields present in the MRI apparatus. Such interference might be caused here by magnetic materials in the encoder or by metallic (albeit nonmagnetic) materials such as aluminum which might produce unwanted eddy currents which affect the gradient fields; both of the foregoing tend to distort the magnetic fields (both d.c. and a.c.—RF and gradient fields) or alternatively affect the accuracy of the MRI apparatus.

OBJECTS AND SUMMARY OF THE INVENTION

It is a general object of the present invention to provide an automatic angle encoding system especially suitable for the MRI apparatus.

In accordance with the above object there is provided an automated angle encoding system for magnetic resonance imaging (MRI) apparatus where total noninterference with the magnetic fields generated by the MRI apparatus is necessary and where the angle between two articulating body parts of a human body in the aperture of the MRI apparatus is being manipulated by an orthopedic positioning device in either a dynamic mode or a kinematic mode and it is necessary to measure the intermittent angles of several positions. The system comprises a substantially nonmetallic, nonmagnetic optical encoder disk connected to the positioning device having an angle of rotation related to the angle of such articulating body parts. A nonmetallic, nonmagnetic casing is provided for the disk having a plurality of nonmagnetic, nonmetallic fiber optic channels for transmitting light and receiving reflected light pulses from the disk to indicate the angle as an absolute quantity. A substantially nonmetallic and nonmagnetic cable carries the fiber optic channels to a receiver/decoder located outside of the said magnetic fields of said MRI apparatus.

BRIEF DESCRIPTION OF THE DRAWINGS

FIG. 4 is a plan view of a single encoding apparatus embodying the present invention as illustrated in simple form in FIG. 2.

FIG. 5 is a cross-sectional view taken along the line 5—5 of FIG. 4.

FIG. 6 is a view taken along the line 6—6 of FIG. 5.

FIG. 7C is a plan view of a glass disk and FIG. 7B is a side view.

FIGS. 10A and 10B are a flow chart for acquiring kinematic scans utilizing the present invention.

DETAILED DESCRIPTION OF THE PREFERRED EMBODIMENT

Figure 1:
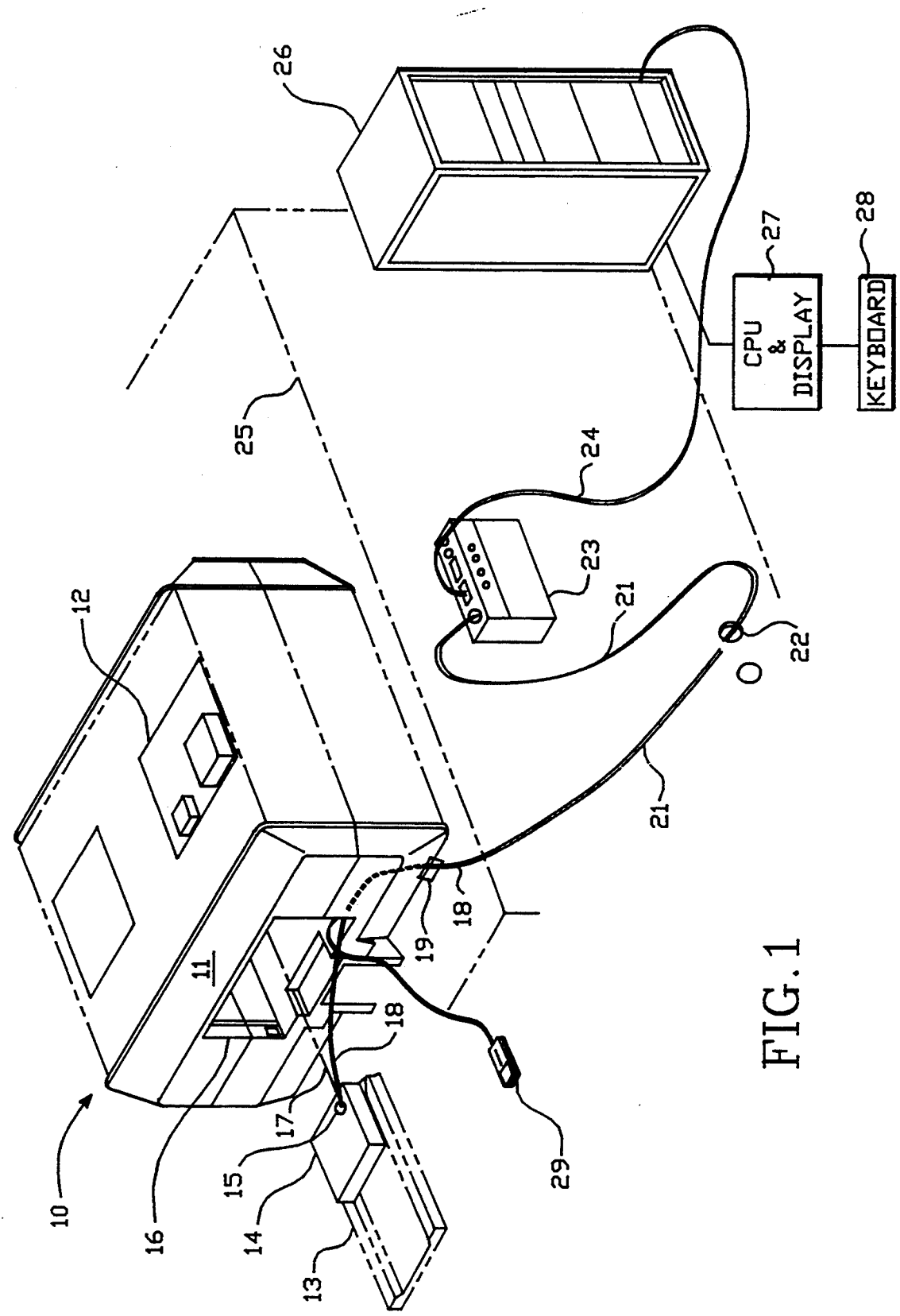
FIG. 1 is a perspective view greatly simplified of an MRI apparatus embodying the present invention.

FIG. 1 illustrates a perspective view of the MRI apparatus 10 which includes a main magnet 11 and equipment designated at 12 to provide necessary radio frequency signals for the well known technique of MRI imaging. The body of the patient is placed upon a sled 13 which includes an orthopedic positioning device 14 with an angle encoder 15. This sled is then moved into the aperture 16, as indicated by the broken line 17, and imaging takes place. Essentially nonmetallic, nonmagnetic cable 18 is connected to the angle encoder 15 for a distance of, for example, fifteen feet, exits the specific MRI apparatus, and is connected by a coupler 19 to a longer fiber optic cable 21 of the same type which extends through waveguide filter 22 in the wall of a screening room 25 in which the MRI apparatus 10 is contained along with its magnetic fields in a manner well known in the art. Cable 21 terminates in an electronics cabinet 23 which decodes the light pulse information (as will be described below) from the angle encoder 15 and converts it to a standard electronic digital code on line 24 and connected to an equipment rack 26. Such equipment rack also would control the MRI. Connected to rack 26 is a central processing unit (CPU) and display 27 along with an operator input keyboard 28. Finally an additional operator input unit 29 is provided in the immediate vicinity of the MRI apparatus; for example, to start scans in the screen room.

Figure 2:
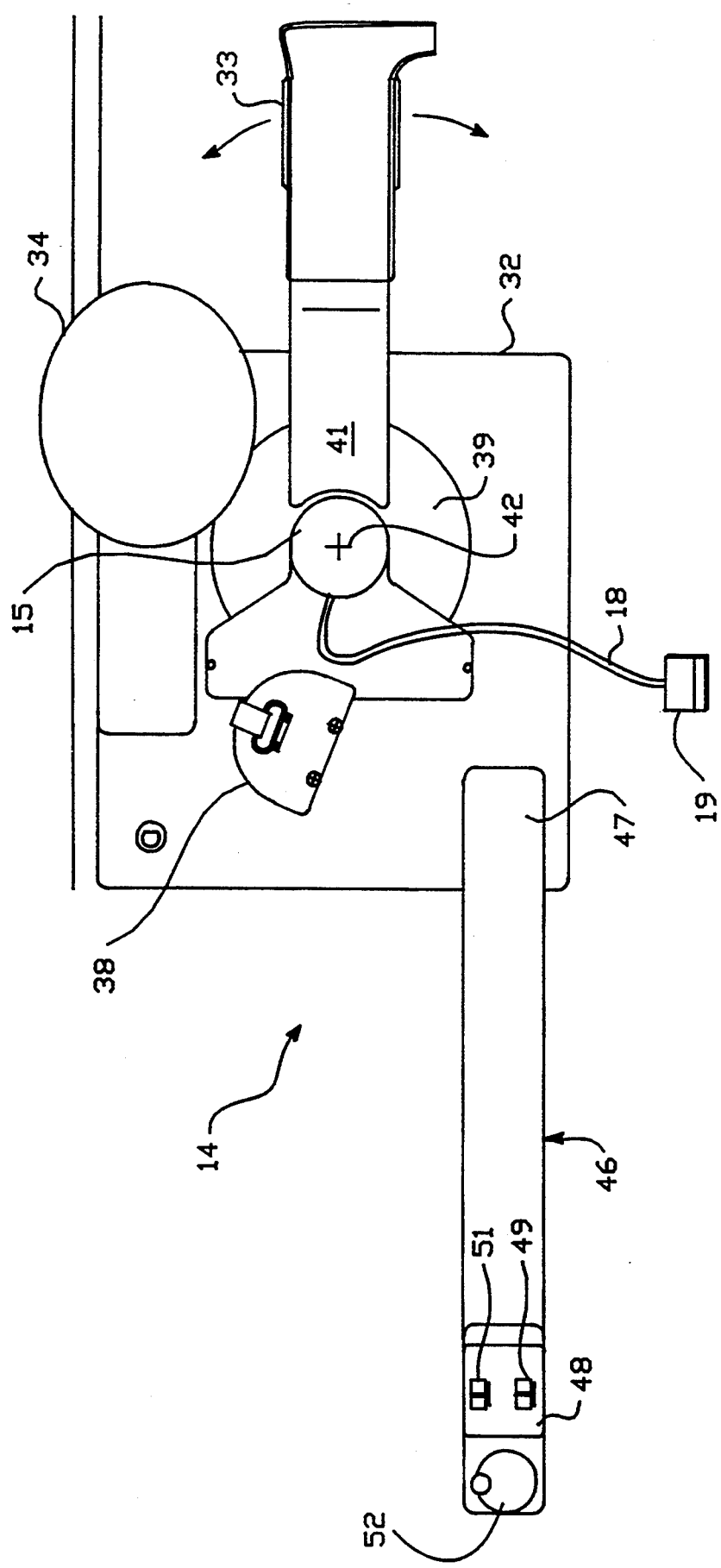
FIG. 2 is a plan view of orthopedic positioning apparatus utilized in FIG. 1 and includes a portion of the encoding system of the present invention.

FIG. 2 illustrates the kinematic positioning device 14 which may be an integral part of the platform 13 or more particularly placed on that sliding platform. The positioning device includes an essentially square base 32 which is placed on the platform 13. Leg rest 34 is affixed to the base 32 and serves to elevate the leg of the patient (the one which is not being imaged) to allow the leg being imaged to move below it. Specifically one leg being imaged is fixed to a calf/foot restraint 33. The elevation provided by the leg rest 34 allows the movement of the calf of one leg to provide for a full flexure of the knee. The foregoing is set out in greater detail in the above referenced co-pending Kriedler et al application.

To provide a repeatable series of images on either a kinematic or dynamic basis of the articulated knee in different flex positions, it necessarily must take place at different moments of time. This is because of the several second time requirement in each MRI image. In order to immobilize the thigh to provide repeatable images, it is clamped by cuff 38 to the platform 32.

The foot/calf restraint 33 is mounted on a rotatable disk 39 by extension 41 of the calf/foot restraint 33 which is fixed to the disk. Disk 39 has a center of rotation at 42 which is essentially the flexure point of the knee. Angle encoder 15 is removably mounted at the center of rotation 42. An optical readout is provided on the fiber optic cable 18 as described below and also as illustrated in FIG. 1.

To incrementally and/or intermittently rotate foot restraint 33 and the disk 39 a driver unit 46 is used having one end 47 affixed to base platform 32. The other end 48 has angle displays 49 and 51 for right and left legs respectively and a manual drive unit 52.

Figure 3:
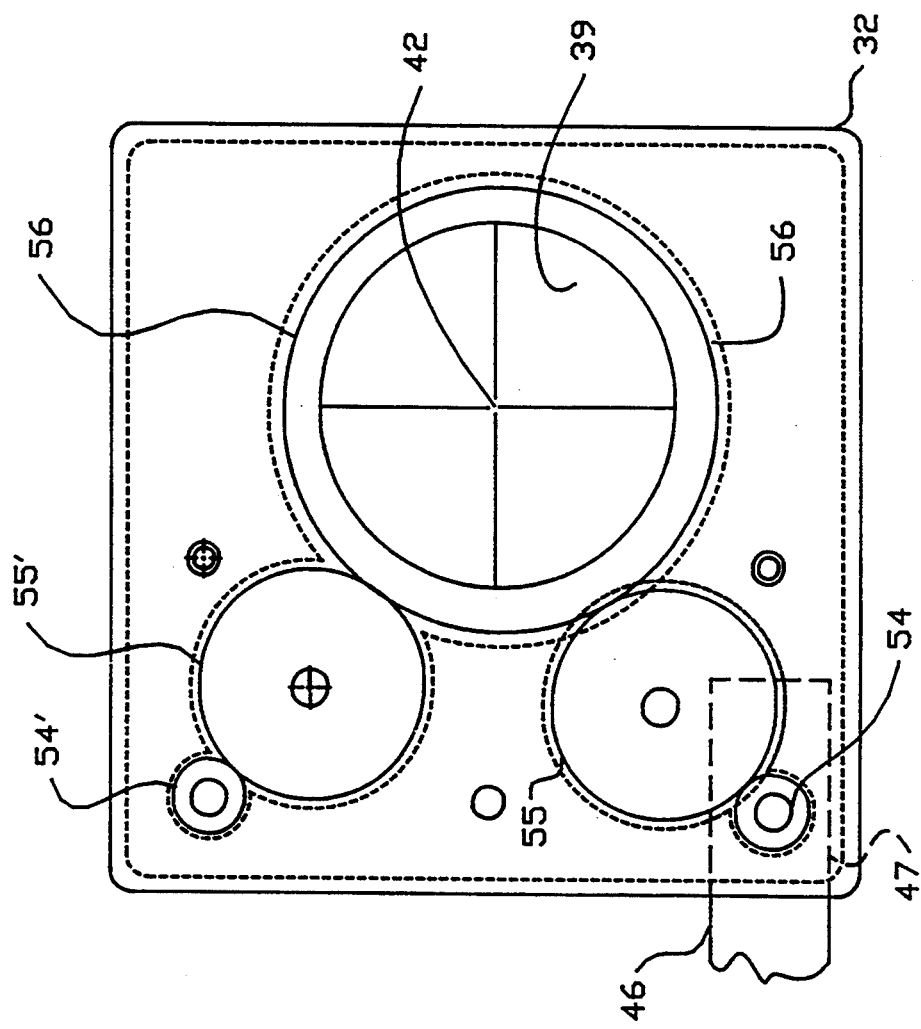
FIG. 3 is a top view in greater detail of a portion of the apparatus shown in FIG. 2.

FIG. 3 illustrates details of the base 32 to which drive unit 46 is attached at 47 and the drive unit driving a spur gear 54 at that end. Gear 54 meshes with an idler gear 55 which in turn meshes with another driven spur gear 56 which is actually a portion of the rotatable disk 39. For reversibility of the system alternate gear 54' and 55' are provided as discussed in the co-pending application. Encoder 15 is mounted (see FIG. 2) by means of a shaft 61 (see FIG. 5) on the center of rotation 42 and is fixed to the platform 32 by a nonmagnetic pin 62. In practice pin 62 may be stainless steel but because of its orientation and small surface area produces only an insignificant eddy current effect, if at all.

FIGS. 4, 5 and 6 show various views and cross-sections of the encoder device 15 and its cable 18 with its coupling 19. Cable 18 consists of several fiber optic information and light carrying channels which are sheathed in nonmagnetic, nonmetallic TEFLON (a trademark) material.

Figure 8:
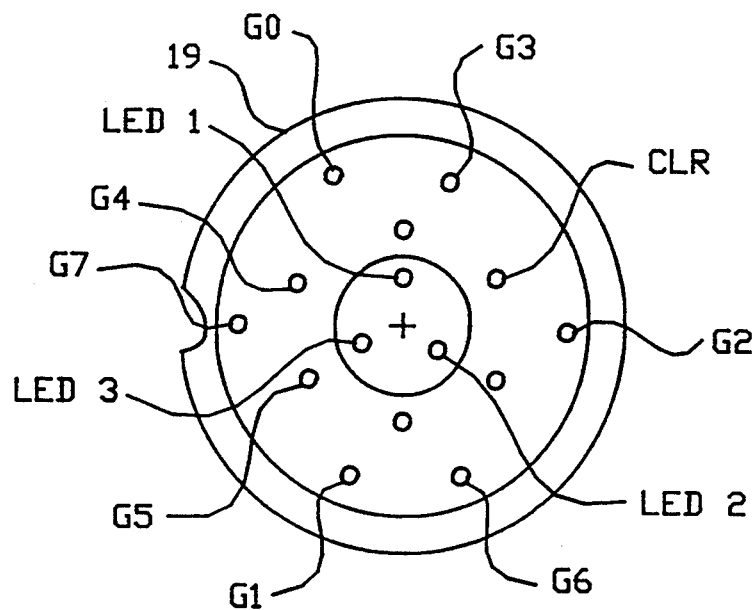
FIG. 8 is an end view of a fiber optic cable utilizing the present invention taken along the line 8—8 of FIG. 4.

FIG. 8 is an end view of the cable 18 and the coupling 19 and shows fiber optic channels G0 through G7 plus a CLR channel and in addition in the center of the cable are three channels carrying light from light emitting diodes which are on a printed circuit board in an encoder unit 23 illustrated in FIG. 1.

Referring again to FIGS. 4, 5 and 6, as discussed above, the shaft 61 is inserted in a matching D-shaped notched center 42 on the disk 39. (See FIG. 3) And then the pin 62 maintains the entire structure in a relatively fixed location on platform 32 while allowing the disk 39 and shaft 61 to move along with the particular limb; in this case, the calf.

FIGS. 7A through 7E is an exploded view of FIG. 5 which includes the top casing 63 of the Delrin plastic material which is, of course, nonmagnetic and nonmetallic. A bottom casing 64 of the same material has an aperture 66 through which a portion of the shaft 61 extends. The other end of the shaft at 62 is in a recess 67 of the top 63. Top 63 also includes a recess 68 in which a glass disk 69 is mounted. On this glass disk is a nonmagnetic chrome pattern (although metallic it has no significant effect because of its limited area and thinness). This pattern, as will be discussed below provides an additional optical code such as a "GRAY" code. And as shown at 71 it is in the form of dots and lines.

Figure 7A:
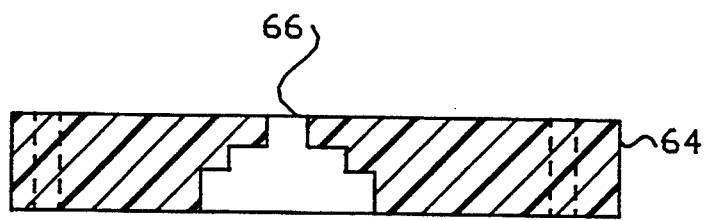
FIGS. 7A through 7E are exploded views of a simplified form of FIG. 5 partially in cross-section and partially in plan view.
Figure 7B:
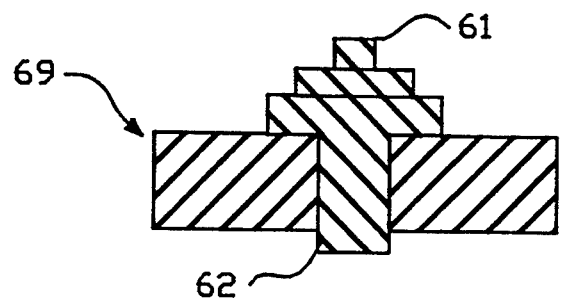
Figure 9:
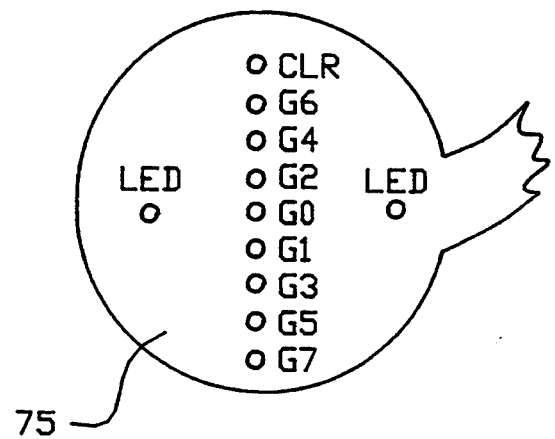
FIG. 9 is a sectional view of the terminating portion of the table of FIG. 8, taken along the line 9—9 of FIG. 6.

The bottom casing 64 shown in FIG. 7A includes a circular groove 72 not shown here but in FIG. 6, which at one end 73 receives a connector 74 which connects into cable 18 and converts the pattern of radially distributed fibers shown in FIG. 8 to the more linear pattern 75 at the other end shown in FIG. 9. The fiber optic cable is embedded by means of epoxy in the circular groove 72.

Figure 7C:
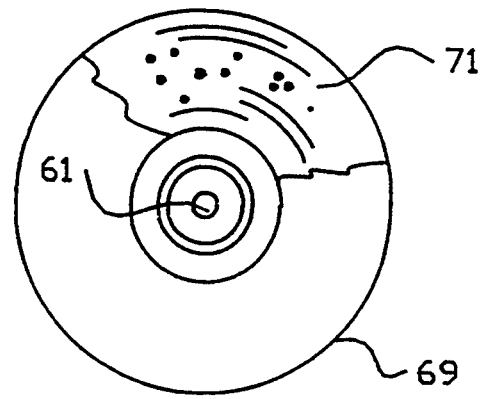
Figure 7D:
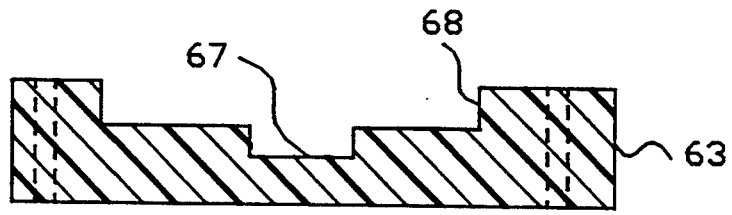
Figure 7E:

In operation the emitting diodes (LED 1,2,3,) (the third is a spare as illustrated in FIG. 9) illuminate the entire glass disk 69 (FIG. 7C). And then the arcuate lines and dots 71 (FIG. 7C) passing by the linear line of fiber optic channels G0 through G7 and CLR illustrated in FIG. 9 provides on the cable 18 a GRAY code. This provides for one revolution of the disk an increasing count which is nonambiguous and also provides direction of rotation. Such GRAY code provides an absolute angle of its rotation from a given start position. Such a disk and coding technique is commercially available and sold by Computer Optical Products of Chatsworth, Calif. However, in its commercial form it is of metal and has other unwanted materials in the encoder. As illustrated in FIG. 7A, the top and bottom casings 62, 64 are fastened together by four plastic or nonmagnetic screws of which 76a and 76b are indicated. FIG. 6 illustrates the remaining two screws 76c and 76d.

The encoder, of course, reads the absolute angle between two articulating body parts such as in the knee between the calf and the thigh. However, other body parts with different type positioners may be used such as for the shoulder, the arm, the neck, etc. Thus in these cases a different orthopedic position or device would be used. Ultimately the angle read by the encoder is translated to numeric form, uploaded to the CPU as illustrated in FIG. 1, and on the kinematic image screen, the angle is indicated either numerically or graphically, or both.

The encoder has the capability of reading the angle of the positioner device in either a kinematic or dynamic mode. In a kinematic mode, the patient's joint is moved to a new angular position while kept in the positioner device. The patient's joint and the device both stop at that new position. The encoder reads the angle of that new position, an angle is acquired, and this process is repeated for new angular positions. Then the various MRI images can be assembled into a movie showing effective joint movement.

In a dynamic mode the patient's joint slowly but continuously moves through a range of angles while kept in the positioner device. The encoder reads a series of angles back when the positioner is in motion and images are acquired simultaneously. The encoder therefore must have a fast enough sampling rate, e.g., 300 Hz, to provide, for example, a 1° angle resolution. At the same time the speed of image acquisition is increased. All parts of the encoder are nonmagnetic and thus will not distort the main magnetic fields of the MRI apparatus. In addition, it is substantially metal free which prevents any distortion of the associated radio frequency fields and minimizes eddy current effects.

For each joint, it is desired to know which direction corresponds to a positive rotation and which corresponds to a negative rotation. Since this is different for different joints, it is necessary to have a means for identifying these joints. With software ID's the operator can identify the particular joint by inputting that ID through the keyboard and CPU. Knowledge of how the encoder fits into a particular device for a particular joint can be programmed into the software as will be illustrated in the flow chart of FIGS. 10A and 10B. The scanning program will then know which direction belongs to a positive rotation and which direction is negative for a particular joint. In addition an encoder offset angle is provided so that there is a positive or negative offset to the absolute angle depending on the body part. Thus the observing physician or MRI operator will not have to interpolate the movement as to whether it is negative or positive and in effect a reference zero starting position will provided. However, the angle offset and absolute angles are permanently stored as part of the patient's record to allow reference to the raw data.

Figure 10A:
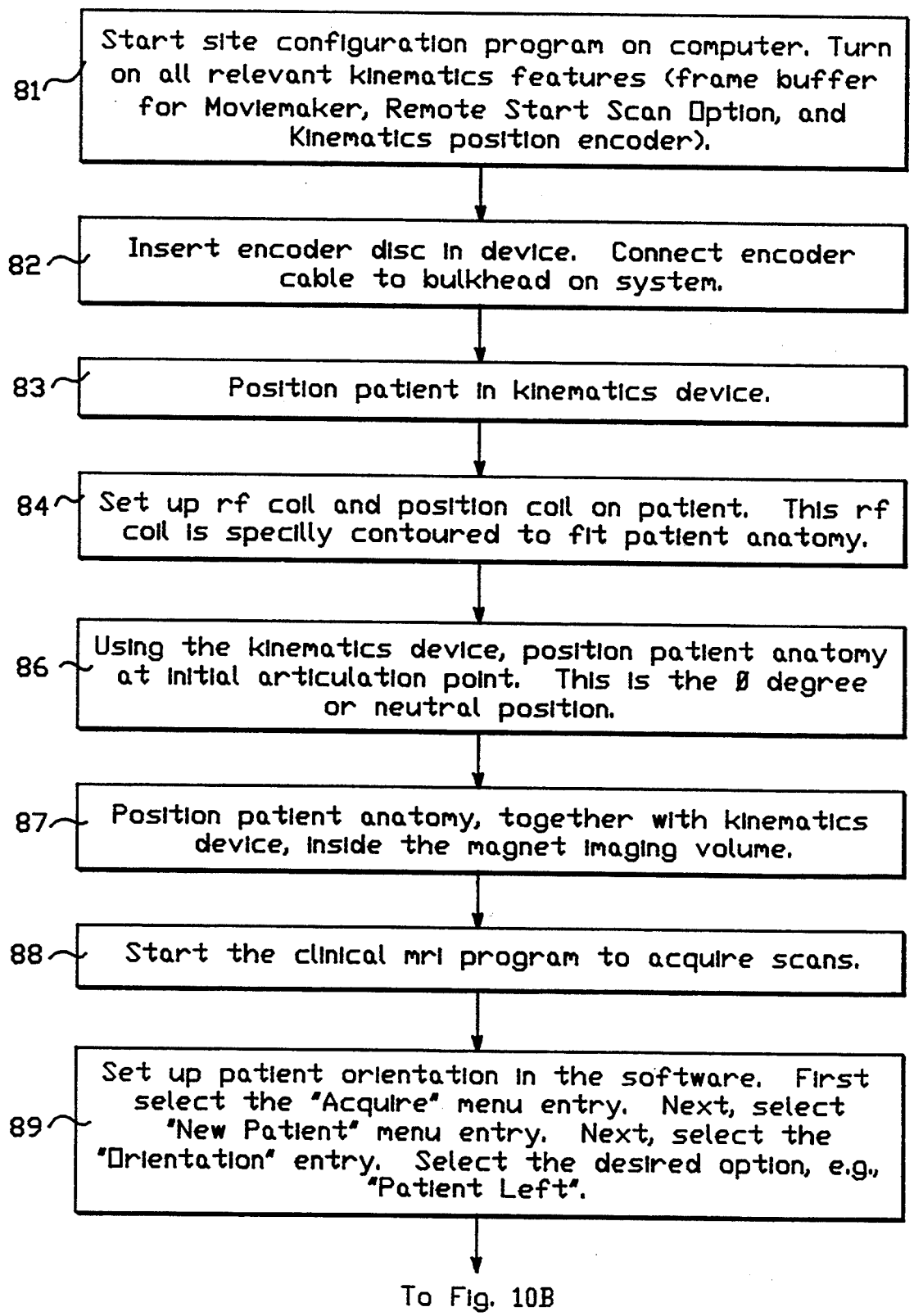

Now referring to FIGS. 10A and 10B, in step 81 all the options for scanning are energized. In step 82 the encoder (which is removable as discussed above since only the shaft 61 is inserted in the movable platform 39) and the encoder cable connection is made through its coupling 19. In step 83 the patient is fastened into the orthopedic positioning device as illustrated in FIG. 2. In step 84 a radio frequency coil of the MRI device is placed on the patient. In the case of the knee this would be a band of material placed around the knee which provides the RF pulses well known in the art for imaging. In step 86 the device is set up for the 0° or neutral position. This information is also stored in the CPU when the type of joint ID is inputted to provide the proper positive or negative offset to the absolute angle read out by the encoder device. Next in steps 87 and 88 the patient is moved by the sled as illustrated in FIG. 1 into the aperture of the MRI and the MRI program started via the CPU. In step 89 how the patient is oriented, for example, left or right leg, etc. is inputted.

In step 91 various kinematic parameters, such as the "left" knee, the correct angle encoder offset are input. Finally the imaging starts at step 92 and test scans are provided to verify the patient's anatomy position. In step 93 imaging protocols are set up and then in step 94 MRI scanning is started and with, for example, use of the remote start scan 29 as illustrated in FIG. 1. In step 96 for each scan an absolute angular position is read and this number after being processed is inserted into the acquired image. Steps 97 and 98 provide for a subsequent scans at different angles and finally at step 99 the images are assembled in a queue for a movie or cine loop. In step 101 the scans are assembled sequentially by a so-called moviemaker software to make a cine loop. This loop is recorded in step 102, the scan information being recorded. From a practical standpoint, the numerical and/or pictorial angle information from the encoder information will appear on that particular set of frames of the cine loop.

The present invention is also useful for MRI study of non-human specimens which involve two articulating parts and a joint; for example, a tube filled with some material being bent.

Thus an automated angle encoder system for MRI apparatus has been provided.

What is claimed is:

1. An automated angle encoding system for magnetic resonance imaging (MRI) apparatus where total noninterference with the magnetic fields generated by the MRI apparatus is necessary including the elimination of eddy currents which would be generated by metallic portions of the encoding system such currents affecting the accuracy of the MRI apparatus, and where the angle between two articulating body parts of a human body in the aperture of the MRI apparatus is being manipulated by an orthopedic positioning device in either a dynamic mode or a kinematic mode and it is necessary to measure the intermittent angles of several positions, said system comprising:

a substantially nonmetallic, nonmagnetic optical encoder disk connected to such positioning device having an angle of rotation related to said angle of such articulating body parts;

a nonmetallic, nonmagnetic casing for said disk having a plurality of nonmagnetic, nonmetallic fiber optic channels for transmitting light and receiving reflected light pulses from said disk to indicate said angle as an absolute quantity;

a substantially nonmetallic and nonmagnetic cable for carrying said fiber optic channels to a receiver/decoder located outside of the said magnetic fields of said MRI apparatus.

2. An encoding system as in claim 1 where said fiber optic channels include as a sheathing, TEFLON.

3. A encoding system as in claim 1 including nonmagnetic and nonmetallic means for fastening said casing around said disk to allow its rotation and nonmagnetic means for also fastening said casing to a relatively fixed portion of said MRI apparatus, said disk rotating relative to said fixed portion.

4. An encoding system as in claim 1 including a central processing unit outside of said magnetic fields for receiving information from said cable carried by said fiber optic channels and for providing in response to said information, numeric data corresponding to said angle of articulation.

5. An encoding system as in claim 4 where said central processing unit provides means for providing a constant positive or negative offset angle to said absolute angle, said offset angle being related to the type of orthopedic articulated body part including the knee, the arm, the neck, and the shoulder, and where said central processing unit provides in response to the type of body part and whether it is a left or right body part including a knee, or elbow or shoulder, a definition of positive or negative movement.

6. An automated angle encoding system for magnetic resonance imaging (MRI) apparatus where total noninterference with the magnetic fields generated by the MRI apparatus is necessary and where the angle between two articulating parts in the aperture of the MRI apparatus is being manipulated by a positioning device in either a dynamic mode or a kinematic mode and it is necessary to measure the intermittent angles of several positions, said system comprising:

a substantially nonmetallic, nonmagnetic optical encoder disk connected to such positioning device having an angle of rotation related to said angle of such articulating parts;

a nonmetallic, nonmagnetic casing for said disk having a plurality of nonmagnetic, nonmetallic fiber optic channels for transmitting light and receiving reflected light pulses from said disk to indicate said angle as an absolute quantity;

a substantially nonmetallic and nonmagnetic cable for carrying said fiber optic channels to a receiver/decoder located outside of the said magnetic fields of said MRI apparatus.

* * * * *